United States Patent [19]

Douglas

[11] Patent Number: 5,104,644

[45] Date of Patent: Apr. 14, 1992

[54] MOUTHRINSE COMPOSITION

[75] Inventor: Jerry A. Douglas, Harrisburg, Ill.

[73] Assignee: 7-L Corporation, Harrisburg, Ill.

[21] Appl. No.: 603,570

[22] Filed: Oct. 25, 1990

Related U.S. Application Data

[63] Continuation-in-part of Ser. No. 476,153, Feb. 7, 1990, abandoned.

[51] Int. Cl.$^5$ ............... A61K 7/16; A61K 7/20; A61K 33/40; A61K 33/30
[52] U.S. Cl. ........................... 424/53; 424/49; 424/613; 424/616; 424/641; 424/642
[58] Field of Search ............ 424/49, 53, 613–616, 424/641, 642

[56] References Cited

U.S. PATENT DOCUMENTS

| | | | |
|---|---|---|---|
| 1,275,275 | 8/1918 | Levinson | 424/55 |
| 2,556,567 | 6/1951 | Wright | 424/642 |
| 2,649,398 | 8/1953 | Wright et al. | 424/642 |
| 3,317,372 | 5/1967 | Hart | 424/642 |
| 3,887,704 | 6/1975 | Lichtenstein | 424/643 |
| 4,100,269 | 7/1978 | Pader | 424/642 |
| 4,160,821 | 7/1979 | Sipos | 424/642 |
| 4,226,851 | 10/1980 | Sompayrac | 424/53 |
| 4,339,432 | 7/1982 | Ritchey et al. | 424/54 |
| 4,395,398 | 7/1983 | Yamamoto | 424/642 |
| 4,406,882 | 9/1983 | Turner et al. | 424/55 |
| 4,425,325 | 1/1984 | Ritchey et al. | 424/54 |
| 4,431,631 | 2/1984 | Clipper et al. | 424/53 |
| 4,477,438 | 10/1984 | Willcockson | 424/616 |
| 4,522,806 | 6/1985 | Muhlemann et al. | 424/642 |
| 4,537,778 | 8/1985 | Clipper et al. | 424/53 |
| 4,568,540 | 2/1986 | Asano et al. | 424/642 |
| 4,647,452 | 3/1987 | Ritchey et al. | 424/642 |
| 4,684,517 | 8/1987 | Clipper et al. | 424/53 |
| 4,895,727 | 1/1990 | Allen | 424/642 |
| 4,937,066 | 6/1990 | Vlock | 424/613 |
| 4,961,923 | 10/1990 | Heyde | 424/49 |
| 4,980,152 | 12/1990 | Frazier et al. | 424/53 |
| 4,992,259 | 2/1991 | Schiraldi et al. | 424/642 |

*Primary Examiner*—Shep K. Rose
*Attorney, Agent, or Firm*—Senniger, Powers, Leavitt & Roedel

[57] ABSTRACT

A mouthrinse preparation containing about 0.5 to about 3% hydrogen peroxide, zinc chloride, sodium lauryl sulfate, and sodium citrate in amounts sufficient to provide antiplaque, antibacterial, astringent, and anticoagulant properties.

6 Claims, No Drawings

MOUTHRINSE COMPOSITION

This application is a continuation-in-part of application U.S. Ser. No. 07/476,153, filed Feb. 7, 1990, now abandoned.

BACKGROUND OF THE INVENTION

This invention relates to mouthrinse compositions and particularly relates to a mouthrinse composition which is capable of killing bacteria responsible for the dental disease process, for restoring the edematous tissue to a normal state, for checking the inflammatory process which is the precipitating factor in marginal gingivitis, and for healing hemorragic tissue.

It is important in maintaining good health to have a healthy oral cavity. A mouthrinse is one of the aids that has been found to be effective in controlling the etiological factors responsible for initiating the disease process of the oral cavity. By controlling the etiological factors, microbiota, local factors, plaque and inflammation, individuals can enhance their chances of remaining free of dental diseases which can contribute to the premature loss of their primary or permanent dentition and even have an adverse effect on their general health.

Accordingly, one of the principal objects of the present invention is to provide a mouthrinse which includes hydrogen peroxide as a principal active ingredient. The hydrogen peroxide has an effect on anaerobic organisms and it also helps remove those microbiota by its mechanical actions of bubbling and foaming. This same action helps to remove local factors.

Another principal object is to incorporate an astringent in the mouthrinse in combination with hydrogen peroxide which helps edematous gingiva return to a more normal state. The preferred astringent is zinc chloride which I feel also has the ability to work as a desensitizer and which also has antiplaque activity. Due to its ability to completely disrupt the microbiota's metabolic activity thru the inhibition of the essential enzymes for the glycolysis of the cell, the reproduction of the cell, the disruption of the energy process of the cell, and the alteration of the living matter of the cell, cytoplasm.

Still a further object of the invention is to incorporate an anticoagulant, preferably sodium citrate, into a preventive mouthrinse to help heal the hemorragic tissue. Hemorrage is one of the first signs of periodontal disease and the anticoagulant helps the exposed capillaries in the wall of the gingival sulcus repair themselves, thus helping the issue repair itself. Sodium citrate also helps inhibit inflammation due to its ability to inhibit the inflammatory initiators by altering the metabolism of anachidonic and of the microbiota. Sodium citrate also complexes the heavy metal ions making them more accessible to cell enzymes, thus accelerating the inhibitory effects of zinc in the cell intra structure.

A still further objective is to incorporate a surfactant such as sodium lauryl sulfate into the composition to further reduce the growth of plaque in the human mouth, particularly in combination with zinc chloride. Sodium lauryl sulfate also has antimicrobial ability as well as serving as a surfactant. This chemical makes the cell walls more permeable interferes with the glycolysis of the cell, enhances protein denaturation, and causes vital constituents essential for normal cell function to leak as a result of the increased permeability of the cell wall from the action of sodium lauryl sulfate.

Still another objective is to provide special mouthrinses with stronger concentrations of zinc chloride for orthodontic and periodontic applications.

These and other objects and advantages will become apparent hereinafter.

SUMMARY OF THE INVENTION

The invention comprises a mouthrinse which includes as a principal active ingredient hydrogen peroxide in an alcoholic aqueous base. The invention also consists in the compositions and the arrangements and combinations of ingredients hereinafter described and claimed.

DETAILED DESCRIPTION

In connection with the specific composition which will be described and claimed hereinafter, it will be helpful to initially have a discussion of the factors involved in periodontal disease. These factors include bacteria, dental plaque, gingivits, and inflammation.

| BACTERIA ASSOCIATED WITH PERIODONTAL DISEASE | |
|---|---|
| Actinobacillus | Campylobacter |
| actinomycetemcomitans | concisus |
| Bacteroides | Cedecea lagagei |
| asacchrolyticus | Eikenella corrodens |
| buccae | Fusobacterium |
| capillus | gonidiaformans |
| capillosis | mortiferum |
| corporis | nucleatum |
| levii | periodonticum |
| denticola | Haemophilus |
| endodontalis | aphrophilus |
| forsythus | influenzae |
| gingivalis | haemolyticus |
| gracilis | parahaemolyticus |
| intermedius | parainfluenzae |
| loeschei | paraphrophilus |
| melaninogenicus | segnis |
| oralis | Peptostreptococcus |
| oris | micros |
| Capnocytophaga | Selenomonas sputigena |
| gingivalis | Veilonella |
| ochracea | atypica |
| sputigena | vulva |
| | Wolinella |
| | curva |
| | recta |
| | Streptococcus |
| | intermedius |
| | mitis |
| | mutans |
| | salivarius |
| | sanguis |
| | Actinomyces viscosus |
| | Candida albicans |

The complexity of the plaque microbiota can be seen in gram-stained smears in which gram-positive and gram-negative can be distinguished as well as various morphologic types (cocci, rods, fusiforms, filaments, spirilia, spirochetes).

The gram-positive faculative cocci belong to the genera, Streptococcus and Staphylococcus. Staphylococci usually comprise no more than 1% or 2% of the gingival sulcus microbiota, whereas, Streptococci comprise 25% to 30%. Streptococcus mutans and *Streptococcus sanguis* of this group are present in large numbers in plaque colonies.

The gram-positive faculative rods make up less than 25% of the microorganisms of plaque. They comprise members of the genera, Corynebacterium, Nocardia, Actinomyces, Bacterionema, and Lactobacillus. One species, *actinomyces viscous*, has been shown to cause dental disease and produce a form of periodontal disease.

Gram-positive anaerobic rods constitute about 20% of the gingival microbiota. They belong to the genera, Corynebacterium, Propionibacterium and Actinomyces. One species, *Actinomyces naeslundi*, can induce plaque formation and form a periodontal disease in germ-free animals.

Varying numbers of gram-negative anaerobic rods are present in the gingival sulcus. These belong to the genera, Bacteriodes, Fusobacterium, Vibrio, Selenomanas and Leptothrix. Gram-negative anaerobic rods may constitute a majority of all genera in the gingival sulcus, especially when there is poor oral hygiene.

Spirochetes constitute a varying percentage of the total flora. In instances of periodontal disease, spirochetes may increase to more than 10% of the total microbiota. The four most prevalent species are: 1) *Treponema denticula*, 2) *Treponema macrodentium*, 3) *Treponema oralis*, and 4) *Borrelia vincenti*.

It is customary to divide bacteria into three categories in regard to their behavior towards molecular oxygen. The anaerobes will grow only when oxygen is rigorously excluded. The faculative anaerobes will grow in the presence or absence of oxygen. The obligatory anaerobes will grow only when supplied with oxygen. The microbiota discussed in the previous paragraphs, that are associated with periodontal disease, can be placed in two groups. One group that is associated with the disease process and the group that is part of the normal flora of the oral cavity. The microorganisms associated with the disease process have to have oxygen excluded to grow. The normal flora requires oxygen to grow.

Microorganisms found in the bacterial plaque have been identified as the principal etiological agents of periodontal disease. Considerable evidence has shown that periodontally diseased sites have a unique microbiota population, very distinct from microbiota found in healthy periodontal sites. The more advanced the disease process is, a greater level of motile rods and spirochetes can be found in proportion to healthy periodontal sites.

The oral haemophili and Actinobacillus actinomycetemcomitans are closely related, gram-negative, non-heme requiring capnophilic bacteria that comprise part of the normal microflora of dental plaque. The pathogenic potential of these organisms is regarded as low, although under certain circumstances they are capable of producing endocarditis, brain abscesses, and orofacial and bite wound infections. Actinomycetemcomitans may also participate synergistically in actinomycotic lesions. Increases in the proportion of actinomycetemcomitans in plaque have been associated with localized juvenile periodontitis, a rapidly advancing form of periodontitis. Such behavior in the oral environment has not been demonstrated in aphrophilus or paraphrophilus, indicating that there may be differences in periodontopathogenic potential among these organisms.

One explanation for this difference in pathogenicity may be a differential susceptibility of these bacteria to toxic oxygen metabolites, especially hydrogen peroxide.

Thus, if you use a rinse in oral irrigation that has heavy concentration of oxygen, antimicrobial agents, anti-inflammatory agents and anti-surface tension agents, you are going to impede the growth process of disease causing microbiota, and furnish oxygen fore the growth of normal flora of the oral cavity, helping the tissues of the oral cavity maintain a normal host-parasite balance.

DENTAL PLAQUE

Oral microbiota organisms that are normal inhabitants of the oral cavity, grow on the surface of teeth and mucous membrances. This growth will adhere to these dental structures if it is allowed to progress. The organisms main habitant is the gingival sulcus around each tooth, the smooth surfaces and pit and fissure anatomy of the clinical crown of the teeth, and the lateral borders of the tongue. The microorganisms that constitute a normal oral environment have no adverse effect on the individual as long as the microorganism-host balance stays normal. On the other hand, the same normal flora may cause periodontal disease if the general resistance of the individual is reduced, or the local factors reduce the resistance of the gingival tissue. Chronic inflammatory agents that precipitate the by-products of the microbiota enzyme system resulting in periodontal disease develops because of the effects of mass populations of anaerobic organisms in the gingival sulcus.

Dental deposits acquired after the eruption of teeth, are placed in six categories; 1) acquired pellicle, 2) stains, 3) dental plaque, 4) dental calculus, 5) materia alba, and 6) food debris. It is very essential to control the deposits on the teeth to maintain good oral hygiene and retain the permanent dentition during a persons natural life.

Dental plaque is composed of bacterial deposits, firmly adhering to the teeth. It can easily be controlled by toothbrushing or oral irrigation with a rinse capable of reducing the masses of microorganisms and their injurious agents that are responsible for the formation of plaque.

It has been clinically and scientifically documented that dental plaque is neither food nor food deposits, nor is it just some bacteria from the mouth. It is a complex metabolically interconnected highly organized bacterial system consisting of dense masses of microorganisms embedded in an intermicrobial matrix. In sufficient concentrations and with the food substances to initiate the metabolic activity of those organisms, the normal balance of the oral cavity becomes disturbed, resulting in the initiation of dental carries or periodontal disease. For this reason alone, any means of oral hygiene to control the activity of the microorganisms of the mouth can result in a reduction of the dental carries process and periodontal disease.

Another form of plaque very common today, due to the busy life style of our society, is materia alba. This combination of bacteria and their injurious products mixed with food particles retained from poor oral hygiene, forms a white soft mass of the gingiva. Materia alba is not as complex as dental plaque, but has the potential to produce tissue reactive by-products which may contribute to the gingival disease process. Materia alba can easily be removed by the proper type of oral rinse. Dental rinses that have the ability to inhibit the microbiota from producing their by-products or inhibiting the enzymes of the microbioat enhances the oral environment for a more conducive host-parasite balance.

GINGIVITIS

Gingivitis or inflammation of the gingiva is almost always present in all forms of gingival disease, because the local irritants that cause inflammation, dental plaque, materia alba, calculus and microorganisms with their injurious products, are almost always present in the oral cavity. The very essential reason all people should use effective health aids to combat the four major irritants of inflammation, is unchecked inflammation progresses to degenerative, necrotic, and proliferative changes in the gingival tissue, resulting in damage to the supporting tissue of the teeth. The damage depends on the duration the inflammatory process has been allowed to go untreated.

Almost all individuals have the primary change in the gingivae, associated with the inflammatory process. The inflamed, edematous, hemorragic tissue in isolated areas of the oral cavity, due to one or more of the local irritants that precipitate the inflammatory process, can result in tissue damage, alteration of the taste perception and if severe enough, chronic infection.

Chronic gingivitis is a conflict between destruction and repair. Persistent local irritants injure the gingiva, prolong inflammation and provoke abnormal vascular permeability and exudation. At the same time, however, new connective tissue, cells and fibers, and new blood vessels are formed in a continuous effort to repair the tissue damage. The interaction between the destruction and repair, affects the color, size, consistency and surface texture of the gingiva.

Proper diet, regular teeth brushing, and oral irrigation are the best defense for gingivitis. Oral irrigation with a mouthrinse that can oxygenate the diseased tissue has a bacteriocidal effect on the microorganisms associated with the inflammatory process and dental plaque. If the mouthrinse contains an astringent, it will have a positive effect on the edematous tissue, and help flush the gingival sulcus around each tooth. Such mouthrinse is an effective aid in checking the inflammation process, responsible for gingivitis, thus, helping to restore a normal host-parasite environment and allow the gingiva to return to its normal color, texture and shape.

Gingivitis requires the physical association of certain streptococcus and actinomyces species with the tooth surface. This may lead to the colonization of other microbiota such as fusobacterial, veillonelea, and trepomemes as well as other bacteria which produce strong irritants such as prodionic and butyric acids. This reaction may allow the emergence of less facultative species as *S. anginosus* and *A. odontolyticus*. Severe gingivitis can exist only as the result of the activity of the microbiota of dental plaque which allows the by-products of these disease initiating bacteria to gain access to the dental tissues surrounding the teeth by causing the epithelial lining of the gingival sulcus to breakdown. The microbiota that initiates the dental disease process produces enzymes and by-products that continues to destroy the dental tissue adjacent to them and if the etiological factors that initiate this process is not removed, the microbiota will produce in vast numbers enabling the destruction of dental tissue to invade deeper structures. Once this happens, a series of inflammatory changes occur. In other words, once the gingivitis starts, it will become a domino effect if the etiological factors responsible are not checked or eliminated. Thus if a dental rinse is used that has the ability to inhibit the inflammatory initiators of the microbiota responsible for this process, gingivitis, you enhance the oral environments ability to maintain the proper bacterial balance.

INFLAMMATION

The majority of periodontal diseases are inflammatory, as evidenced by the dense cellular infiltrate in the gingival corium, subjactent to the gingival pocket around each tooth, and by the exudate, which contains polymorphonuclear leukocytes and inflammatory serum components, emanating from the gingival pocket around each tooth. The intimate contact of plaque with the contiguous gingiva, makes such inflammation readily understandable. Inflammation soon superimposes itself even in these periodontal diseases that are not primarily inflammatory. For this reason, it is essential to control inflammation in the oral cavity.

The gross stages in the inflammatory process are:

a) Injury to tissues, initiating the inflammatory reaction.

b) Hyperemia, caused by dilatation of capillaries and venules.

c) Increased vascular permeability and the accumulation of inflammatory exudate containing leukocytes, macrophages and lymphocytes.

d) Breakdown of the irritant causing the injury to the tissue.

e) Initiation of tissue repair.

The primary causes of inflammation in the oral cavity are dental plaque, materia alba, calculus and improper restorative restorations. Inflammation is extremely common in almost all oral cavities, due to the four common causes and the microorganisms with their injurious products that are always present in the gingival environment. Inflammation can also be a result of a systemic disorder.

Thus, it becomes very evident that the control of inflammation, is very essential in maintaining good oral hygiene. Experimental results have shown that a strictly healthy gingiva at the clinical level examined under a microscope, is void of inflammation. In such microscopic exams, the sulcular epithelium is almost entirely free of inflammatory cells.

Inflammation is a normal tissue defense, therefore, it should not be inhibited completely. On the other hand, it should be intercepted early to prevent its chronic condition from causing permanent tissue damage. Chronic inflammation results in constant pressure on the alveolar process, which results in chronic bone loss, one of the most prevalent etiological factors contributing to loss of the permanent dentition. That is why it is very essential to control the etiological factors responsible for the initiation of the inflammatory process, a) plaque, b) materia alba, c) calculus, and d) improper dental restorations.

SPECIFIC COMPOSITION

The preferred composition of the present invention comprises a combination of an oxygen releasing agent, that also works as an astringent and anti-inflammatory agent, preferably hydrogen peroxide; an antimicrobial, preferably zinc chloride which also has antiplaque effect; and an astringent, anticoagulent, and anti-inflammatory agent, preferably sodium citrate, in an alcoholic aqueous base which has, in addition, certain flavorings, coloring agents. The composition also preferably includes a surfactant and surface tension lowering agent, preferably sodium lauryl sulfate which also enhances the anti-bacterial action of zinc salts.

The hydrogen peroxide is used in the amount of about 0.5 to about 3% by weight of the overall composition. Hydrogen peroxide releases molecular hydrogen in the presence of tissue enzymes, catalase and peroxidase.

This chemical reaction happens instantly when the hydrogen peroxide contacts the enzymes of the microbiota and the chemical reaction proceeds very rapidly. The reaction exposes the tissues and oral microbiota to the released oxygen for a short period of time and the oxygen has bactericidal effect on the anaerobic organism associated with dental diseases. The bubbling and foaming action of hydrogen peroxide as the oxygen is released exerts a mechanical action which is useful in removing food particles and microbiota from the gingival sulcus and dental plaque. It also helps clean the pit and fissure anatomy of the clinical crown. Thus, it is an effective aid in reducing the caries process.

In addition, hydrogen peroxide kills certain anaerobic bacteria in cultures because of its oxidizing power. This action gives the tissues and normal flora of the oral cavity a boost of oxygen that is essential for their normal function. Hydrogen peroxide is a normal ingredient of the oral cavity. The antimicrobial preferably is zinc chloride and it preferably is present in an amount of at least about 0.02% and preferably about 0.02 to about 0.04% by weight of the composition in the regular mouthrinse. The periodontal mouthrinse has up to about 0.80%. The zinc chloride helps restore the edematous tissue to a normal state and also helps check the inflammatory process which is the precipitating factor in marginal gingivitis due to its ability to completely alter the metabolic activity of the pathogenic microbiota.

Zinc salts also have an antiplaque effect and beneficial effects on the microbiota that compose the complex intermatrix of dental plaque. Zinc remains in dental plaque several hours after rinsing. This is possible due to the ability of zinc chloride to bind itself to the cell wall of the microbiota that make up the intermatrix of dental plaque. The attachment of zinc chloride to the cell walls prevents the microbiota from adhering to each other and attaching themselves to tooth structure. Zinc chloride, by its adhesion to the microbiota of the plaque, disrupts the metabolic activity of the cells, thus reducing the growth rate of the cells. By preventing the microbiota from adhering to each other and impeding their growth rate you prevent dental plaque from becoming the complex intermatrix of microbiota along with their enzyme and by-products from attaching to tooth structure, thus improving the chances for a more conducive host/parasite balance.

Zinc ions have been documented to inhibit the active sugar transport of streptococcus mutans, glucose uptake, and metabolism of streptococcus sobrinus. Zinc ions may also inhibit enzyme systems of the microbiota of plaque by displacing magnesium ions essential for enzymatic activity of the plaque. It is also possible that the antimicrobial action of zinc is due to a nonspecific interaction with the cell proteins of the plaque microbiota.

Zinc has also been shown to inhibit acid production by the microbiota of plaque due to its ability to impede the sugar transport by the streptococcus mutans of the dental plaque. This reduces the acidogenicity of plaque, thus impeding decalcification.

Zinc ions may interfere with the transport and oxidation of substrates of the microbiota of plaque by inhibiting the energy process necessary for transport of these substrates. This may occur by the zinc ion blocking the electron transport chain or inhibiting the formation of ATP. Zinc may also cause a conformational change in the enzymes or protein of plaque microbiota which causes the enzymes or protein to become inactive in the transport mechanism of the cells.

Preferably the surfactant is sodium lauryl sulfate, which is one of the most widely used synthetic detergents that helps in the formulation of mouthrinses, due to its ability to function as a surfactant and lower surface tension. When mixed with certain chemicals, most notable the zinc salts, sodium lauryl sulfate enhances the bacterial activity of those chemicals, plus having bacterial inhibitory ability of its own integrity.

Sodium lauryl sulfate has been shown to act on the cell walls making them more permeable. Sodium lauryl sulfate is a denaturing agent with a high affinity for cell proteins. This affinity, along with absorption of the molecule to the microbiota surfaces, causes interference with cell integrity. Sodium lauryl sulfate inhibits the enzyme, glucosyltransferase from streptococcus mutans, and the glucose phosphotransferase enzyme system in the cell membranes of streptococcus sobrinus. This inhibitory action helps reduce the acidogenicity of plaque by interfering with the sugar transfer of the plaque microbiota. This action of sodium lauryl sulfate could partially explain why zinc salts have a three fold effect on plaque microbiota when used in conjunction with sodium lauryl sulfate. Zinc salts are retained by microbiota cells for up to 10 hours after rinsing with a mouthrinse with sufficient concentrations of zinc salts. This is due to the ability of zinc to adhere to cell walls. This progress could be enhanced by the ability of sodium lauryl sulfate to make the cell walls more permeable.

It is not clear why sodium lauryl sulfate helps prevent plaque from forming. Some clinicians claim sodium lauryl sulfate has a high affinity for calcium, hydroxyapatite powder and tooth enamel, and this high affinity prevents plaque from attaching to tooth surfaces. Others feel sodium lauryl sulfate prevents the adhesion of plaque to tooth enamel due to the binding of sodium lauryl sulfate electrostatically to the tooth surface and oral mucosa through calcium bridges. Sodium lauryl sulfate molecules may compete with negatively charged bacterial surfaces for binding sites and thus interfere with microbiota adhesion to tooth enamel and interfere with the microbiota of plaque adhering to each other, preventing the complex matrix of bacteria from maturing into complete dental plaque.

The increased plaque inhibiting ability of zinc salts and sodium lauryl sulfate when used together may be due to the formation of sodium zinc lauryl sulfate complexes.

Sodium lauryl sulfate is used in an amount of at least about 0.04% by weight and preferably 0.04–0.08% in the regular mouthwash. In the orthodontic and periodontal mouthrinses up to about 0.25% may be used.

Preferably the anticoagulant and anti-inflammatory is sodium citrate which is preferably present in an amount of at least about 0.03% by weight of the composition and preferably about 0.03–0.06% in the regular mouthwash. In the periodonal and orthodontic mouthrinses up to about 0.20% can be used. The sodium citrate helps to heal the hemorragic tissue. Hemorrage is one of the first signs of periodontal disease and the sodium citrate helps the exposed capillaries in the wall of the gingival sulcus repair themselves which helps the tissue repair itself.

The alcohol in the composition has a sterilizing effect on the mouth and the other ingredients are used to produce the final desired pH of about 3.5 to about 4.0 in the regular mouthrinse as well as being added for taste and color. Some of these ingredients can be varied depending on the particular taste and color desired in the final mouthwash. The pH of the periodontal mouthrinse is about 3.5–5.5 and the pH of the orthodontal mouthrinse can be 6–7.

Following is a specific preferred composition of the present invention.

EXAMPLE NO. 1

| | |
|---|---|
| Disodium Edta | 5.5 lb. |
| Zinc Chloride USP | 2 lb. |
| Hydrochloric Acid | 15 ml. |
| Glycerin | 34 gal. |
| FDC Green #3 | 4.5 g |
| DC Yellow #10 | 17.5 g |
| Stepanol WA-100 | 7.5 lb. |
| Sodium Citrate | 3 lb. |
| Citric Acid | 10 g. |
| Sodium Saccharin | 2 lb. 12 oz. |
| SD Alcohol 38 B-2 | 22.5 gal. |
| Poloxamer 407 | 50 lb. |
| Peppermint Oil | 1.5 lb. |
| Menthol | 4 lb. |
| SD Alcohol 38 B-2 | 20.5 gal. |
| Sodium Hydroxide Pellets | 1 lb. 2 oz. |
| Deionized Water | qs. to 1200 gal. |
| Hydrogen Peroxide - 3% soln. | 250 gal. |

The disodium edta is a kelating agent used to combine the various minerals in the water. The hydrochloric acid is used to maintain the pH of the composition at the desired level. The glycerin is used as a humectant or as a moistening agent or dilutant. The Stephanol WA-100 is a surfactant (sodium lauryl sulfate) used to break surface tension. Citric acid is an acid used for demineralization and as a stimulant for reattachment of connective tissue to tooth structure. Sodium saccharin is a non-caloric sweetner. Poloxamer 407 is used to keep essential oil soluble. The sodium hydroxide is used for pH balance and peppermint oil and menthol are flavoring agents. SD Alcohol 38 is a federally controlled ethyl alcohol 92%, denatured and approved for mouthrinse use.

Following is a list of the ingredients in a regular mouthrinse:

| REGULAR MOUTHRINSE | |
|---|---|
| | % by weight |
| Ethanol | 2.0–3.0 |
| Glycerin | 2.5–3.5 |
| Poloxamer 407 | 0.25–0.50 |
| Sodium Lauryl Sulfate | 0.04–0.08 |
| Sodium Saccharin | 0.02–0.05 |
| Sodium Citrate | 0.03–0.06 |
| Citric Acid | 0.01–0.05 |
| Zinc Chloride | 0.02–0.04 |
| Flavors | 0.02–0.04 |
| D & C Approved Dyes | Q.S. |
| Disodium Eta | 0.03–0.05 |
| Hydrogen Peroxide | 0.05–3.0 |
| Purified Water | Q.S. to Volume pH 3.5/4.0 |

EXAMPLE NO. 2

This invention also is useful in orthodontic work where the braces tend to accentuate the formation of plaque. The composition for this application has increased amounts of sodium citrate, zinc chloride and sodium lauryl sulfate.

| SPECIAL ORTHODONTIC MOUTHRINSE | |
|---|---|
| Ethanol | 2.5 to 3.5 |
| Glycerin | 5.5 to 7.5 |
| Poloxamer 407 | 0.85 to 1.25 |
| Sodium Lauryl Sulfate | 0.10 to 0.20 |
| Sodium Saccharin | 0.04 to 0.06 |
| Sodium Citrate | 0.10 to 0.20 |
| Citric Acid | 0.02 to 0.03 |
| Zinc Chloride | .075 to 0.10 |
| Flavors | 0.10 to 0.15 |
| D & C Approved Dyes | Q.S. |
| Disodium Eta | 0.10 to 0.30 |
| Hydrogen Peroxide | 1.5 to 3.00 |
| Purified Water | Q.S. to Volume pH 6.0/7.0 |

EXAMPLE NO. 3

A composition specifically for periodontic use has a much larger concentration of zinc chloride to combat the gram negative environment of the mouth with periodontal disease.

| SPECIAL PERIODONTAL MOUTHRINSE | |
|---|---|
| Ethanol | 2.5 to 3.50 |
| Glycerin | 6.5 to 7.50 |
| Poloxamer 407 | 0.85 to 1.25 |
| Sodium Lauryl Sulfate | 0.15 to 0.25 |
| Sodium Saccharin | 0.04 to 0.06 |
| Sodium Citrate | 0.01 to 0.20 |
| Citric Acid | 0.02 to 0.03 |
| Zinc Chloride | 0.60 to 0.80 |
| Flavors | 0.10 to 0.25 |
| D & C Approved Dyes | Q.S. |
| Disodium Eta | 0.10 to 0.30 |
| Hydrogen Peroxide | 1.5–3.0 |
| Purified Water | Q.S. to Volume 3.5/5.5 |

This invention is intended to cover all changes and modifications of the examples of the invention herein chosen for purposes of disclosure which do not constitute departures from the spirit and scope of the invention.

What is claimed is:

1. A mouthrinse preparation comprising between about 0.5% and about 3.0% by weight hydrogen peroxide, at least about 0.025% by weight zinc chloride, at least about 0.03% sodium citrate, at least about 0.04% by weight sodium lauryl sulfate and between about 2% and about 3.5% by weight ethanol.

2. The mouthrinse preparation of claim 1 wherein the preparation comprises between about 0.025% and about 0.8% by weight zinc chloride.

3. The mouthrinse preparation of claim 1 wherein the preparation comprises between about 0.03% and about 0.2% by weight sodium citrate.

4. The mouthrinse preparation of claim 1 wherein the preparation comprises between about 0.04% and about 0.25% by weight sodium lauryl sulfate.

5. The mouthrinse preparation of claim 1 wherein the preparation comprises between about 0.025% and about 0.8% by weight zinc chloride and between about 0.03% and about 0.2% by weight sodium citrate.

6. The mouthrinse preparation of claim 1 wherein the preparation comprises between about 0.025% and about 0.8% by weight zinc chloride, between about 0.03% and about 0.2% by weight sodium citrate, and between about 0.04% and about 0.25% by weight sodium lauryl sulfate.

* * * * *